United States Patent [19]
Hazelton et al.

[11] Patent Number: 4,880,682
[45] Date of Patent: Nov. 14, 1989

[54] LOW GLOSS FILM AND PROCESS OF MANUFACTURE (FP 1323)

[75] Inventors: Donald R. Hazelton, Chatham, N.J.; Douglas J. Laurent, Houston, Tex.; Lawrence K. Locke, Seabrook, Tex.; William J. Hodgson, Jr., Baytown, Tex.

[73] Assignee: Exxon Chemical Patents Inc., Linden, N.J.

[21] Appl. No.: 171,730

[22] Filed: Mar. 22, 1988

[51] Int. Cl.⁴ .............................................. B32B 27/14
[52] U.S. Cl. ...................................... 428/152; 428/198; 428/332; 428/337; 428/516; 428/517; 428/518
[58] Field of Search ............... 428/152, 195, 198, 409, 428/516, 517, 518, 332, 337

[56] References Cited

U.S. PATENT DOCUMENTS

| | | | |
|---|---|---|---|
| 3,843,478 | 10/1974 | Zuscik | 128/82 |
| 4,522,887 | 6/1985 | Koebisu et al. | 428/516 |
| 4,643,926 | 2/1987 | Mueller | 428/517 |
| 4,769,261 | 9/1988 | Hazelton et al. | 428/213 |

FOREIGN PATENT DOCUMENTS

| | | | |
|---|---|---|---|
| 51-31774 | 6/1976 | Japan . | |
| 51-31773 | 7/1976 | Japan . | |
| 56-11231 | 5/1981 | Japan . | |
| 1125400 | 8/1968 | United Kingdom | 156/229 |
| 1453649 | 10/1976 | United Kingdom | 156/229 |

Primary Examiner—Ellis P. Robinson
Assistant Examiner—P. J. Ryan
Attorney, Agent, or Firm—R. L. Graham; M. E. Wilson

[57] ABSTRACT

A multilayer film comprises a elastomeric core layer and at least one thermoplastic skin layer having a microundulating surface configuration providing the film with a low gloss.

17 Claims, 1 Drawing Sheet

LOW GLOSS FILM AND PROCESS OF MANUFACTURE (FP 1323)

BACKGROUND OF THE INVENTION

This invention relates generally to films useful in a variety of domestic applications in which the properties of elasticity, low gloss, and good "hand" are desirable. Examples of such applications include back sheets for diapers, colostomy bags, elastic garment closures (e.g. sleeve bands, diaper leg bands and waist band), and the like. In one aspect the invention relates to a coextruded film and method of manufacture.

DESCRIPTION OF THE PRIOR ART

Although the film of the present invention, because of its unique properties, may be used in a variety of applications, the disclosure herein will emphasize its application as a diaper back sheet. Film used in diapers and similar absorbent goods such as incontinent garments must possess certain physical properties and certain esthetic propertis for successful marketing. For example, the backsheet of diapers which contain the absorbent material must possess adequate physical properties for durabiilty. Equaly important is the appearance of the diaper for customer appeal. Experience has shown that the diaper must not only possess a matte finish (low gloss) but must also possess the proper "hand" or "feel", and be free of "plastic" noise on handling. The term "hand" and "feel" are frequently used in the textile industry to describe a property of fabric which affects the sense of touch (e.g. rough, plastic, silky, coarse, etc.). Moreover, it is important that the diaper fit comfortably on the wearer and provide secure containment.

The conventional procedure for obtaining matte finish diaper back sheets is by a process in which a cast film is passed through the nip of a pair of rollers, on of which has a pattern engraved roller or a special sanded finish. The film is thus embossed with either a pattern finish or irregular sanded finish, both of which provide low gloss on the film procesed thereby. The conventional embossing process described above has lmitations, particularly with regards to economics. While modern cast lines can produce films at rates up to 1500 feet per minute, the embossing process is limited to line speeds of about 700 feet per minute. Moreover, the "hand" or "feel" of the embossed film is not particularly good.

Low gloss or matte finish films are disclosed extensively in patents and the published literature. See for example Japanese Kokai's Nos. 76 31,773, 76 31,774, 81 11,231, GB No. 1453649, U.S. Pat. Nos. 3,843,478, and 4,522,887.

SUMMARY OF THE INVENTION

It has been surprisingly discovered that a low gloss, elastic, matte finish film possessing exceptional hand and feel is obtained by a coextruded multilayer film comprising an elastomeric core (layer B) and thermoplastic skins (layers A). The core layer B has a substantially flat disposition whereas the thermoplastic skin layers A have a microundulating or rippling configuration. The microundulating configuration not only imparts a matte, low gloss finish to the surface of the composite, but aso improves the film's tactile properties (i.e. "hand" and "feel"). Moreover the rubber core layer of the composite imparts elasticity to the garment thereby providing exceptional fit and containment (if used in a diaper).

The process for producing the film includes generally the steps of (a) coextruding an ABA composite film wherein the skin layers A comprise thermoplastic material and the core layer B comprises elastomeric material; (b) stretching the composite film at least 100% of its original length; and (c) relaxing the stretched film. This process produces a film with the skin layers having microundulations described above. Relaxation of the stretched film causes the rubber core layer to contract more than the thermoplastic skin layers thereby providing an irregular microsurface on the composite structure. In the relaxed stretched condition, the microundulations, while not readily discernable by the naked eye, impart a low gloss and silky feel to the film. (The term "relaxed stretched condition", as used herein, describes the condition of the film after the stretching and relaxation steps of the process.)

The elastomeric core for the ABA structure described above may comprise and/or include a variety of elastomers. The preferred elastomers are polyisobutalene (PIB), butyl rubber, ethylene-propylene copolymer rubber (e.g. EPM or EPDM), block copolymer rubbers (e.g. SBS, SIS, or SEBS), and mixtures of these copolymers. The skin layers are thermoplastics, preferably ethylene copolymers such as ehtylene vinyl acetate (EVA) copolymers.

The relative thickness of the A and B layers of the ABA composite may range within wide limits so long as the stretch/contraction step produces the microundulations which provide a gloss of less than 20, preferably 10 or less. The preferred ranges are as follows:

|   | BROAD RANGE wt % of Total Thickness | PREFERRED RANGE wt % of Total Thickness |
|---|---|---|
| A | 2.5 to 20 | 5 to 15 |
| B | 95 to 60 | 90 to 70 |
| A | 2.5 to 20 | 5 to 15 |

The total thickness of the multilayer film of the present invention is less than 20 mils and preferably 10 mils or less.

The microundulation configuration of the skin layers of the film according to the present invention are to be distinguished from the embossing or sanded finish of the prior art. The irregular surface provided by the former is a result of gathering on a micro scale whereas the latter achieves surface pattern or irregularities by permanent deformation of the film.

DESCRIPTION OF THE PREFERRED EMBODIMENT

Figure 1:
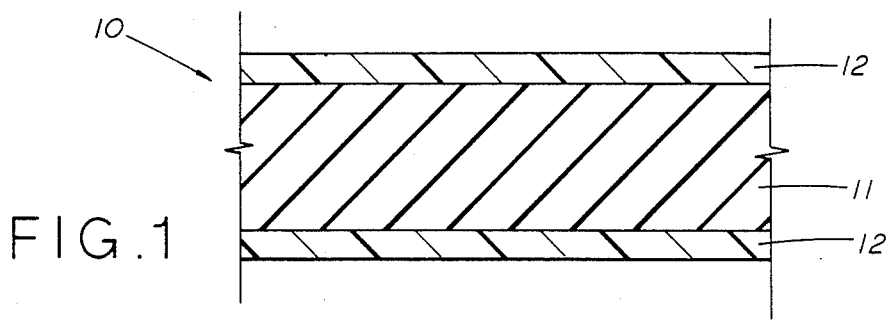
FIG. 1 is a cross sectional view of the three layer film of the present invention.

With reference to FIG. 1, the film 10 of the present invention is a composite comprising an elastomeric core layer 11 and two thermoplastic skin layers 12. This ABA film composite may be manufactured by coextrusion processes (as described in more detail below) and by selective stretching and relaxing to produce the desired surface profile of layers 12 (illustrated in FIG. 2). The film 10 thus produced surprisingly exhibits the following properties which make it ideal for a number of applications:
(1) good strength properties (in both TD and MD)
(2) matte finish
(3) good hand and feel (silky)
(4) quiet nonplastic "noise" (i.e. rustle free)
(5) high elasticity As described in more detail below, the compositions of the elastomeric core layer 11 and thermoplastic skin layers 12 may vary within relatively wide limits, provided that the core and skin layers exhibit differential contraction to produce the microundulating surface. The terms "rubber" and "elastomers" are used interchangeably herein and fit the definition of rubber per ASTM D 1566 which is incorporated herein by reference. Also, the "MD" and "TD" are abbreviations for machine direction and transverse direction which are used in their conventional sense meaning, respectively, the direction in which the film is processed and the direction at right angles therewith.

Elastomeric Core Layer: The rubber core layer 11 must be composed of a rubber which (a) is capable of melt extrusion in the same general temperature range of thermoplastic resin used in the skin layers; (b) can be extended at least 100% of its original length and recover a substantial amount of its extended length (preferably more than 50%); (c) adhere to the skin layer; and (d) permit random separation from the skin at locations generally uniformly distributed across its surface to produce the microudulating surface profile.

The rubbers (elastomeric resins) which can be used in the practice of this invention include both synthetic and natural rubbers; preferably the rubber have a glass transition-temperature (Tg) of less than 0° C. and have a Shore A hardness of 50 or below, preferably 40 or below, or a 100% modulus of 110 kg./cm² or less or a Young's modulus below 1000 kg./cm². Illustrative, non-limiting examples of rubbers suitable for use in the practice of this invention include polyisobutylne (PIB), butyl rubber, halogenated butyl rubber, ethylene propylene rubber (EPM), ethylene-propylene diene rubber (EPDM), plyisoprene, polychloroprene, styrene-butadiene rubber, polybutene copolymers, nitrile rubbers, chlorosulfonated polyethylene, block copolymer rubber, etc.

The block copolymer rubber includes from 50 to 85 wt % of a central block of a rubbery olefin polymer of generally equal proportions of ehtylene and butylene units and terminal blocks of polystyrene (SEBS). A commercially available block copolymer rubber is Kraton sold by Shell Oil Company. Other rubbery copolymers utilize a central block of butadiene (SBS) or isoprene (SIS) instead of the ethylene butylene copolymers. The preferred block copolymer rubbers are the SEBS copolymers having a molecular weight of between about 50,000 to 120,000.

The terms EPM and EPDM are used in the sense of their ASTM designations (ASTM D-1418-72a). EPM is an ethylene-propylene copolymer which can be cross-linked by radiation curing or peroxide curing.

As used in the specification and claims the term "EPDM" means terpolymers of ethylene alphaolefin and non-conjugated diene. The non-conjugated diolefin can be straight chain, branched chain or cyclic hydrocarbon di-olefins having about 6 to about 15 carbon atoms such as:

A. straight chain dienes such as 1,4-hexadiene and 1,6-octadiene;

B. branched chain acrylic dienes such as 5-methyl-1, 4-hexadiene; 3,7-dimethyl1-1,6-octadiene; 3-7-dimethyl1-1, 7-octadiene and the mixed isomers of dihydromyricene and dihydroocinene;

C. single ring alicyclic dienes such as 1,3-cyclopentadiene; 1,4-cyclohexadiene; 1,5-cyclo-octadiene and 1,5-cyclododecadiene;

D. multi-ring alicyclic fused and bridged ring dienes such as tetrahydroindene, methyl, dicyclopentadiene; bicyclo-(2,2,1)-hepta-2, 5-diene; alkenyl, alkyliene, cycloalkenyl and cycloalkylidene norbornenes such as 5-methylene-2-norbornene (MNB), 5-propenyl-2-norbornene, 5-(4-cyclopentenyl)-2-norbornene, 5-cyclohexylidene-2-norbornene, 5-vinyl-norbornene and norbornadiene.

Of the non-conjugated dienes typically used to prepare EPDM terpolyers the preferred dienes are dicyclopentadiene, 1-,4-hexadiene, 5-methyl-2-norbornene and 5-ethylidene-2-norbornene. Particularly preferred diolefins are 5-ethylidene-2-norbornene (ENB) and 1,4-hexadiene.

EPDM elastomers and their general method of manufacture are well known in the art. The preferred EPDM elastomers contain about 20 to about 90 wt % ethylene, more preferably about 30 to 80 wt % ethylene, most preferably about 35 to about 75 wt % ethylene.

The alpha-olefins suitable for use in the preparation of EPDM are preferably $C_3$–$C_{16}$ alpha olefins. Illustrative non-lmiting examples of such alpha olefins are propylene, 1-butene, 1-pentene, 1-hexene, 1-octene and 1-dodecene. The alpha olefin is generally incorporated into the EPDM polymer at about 10 to about 80 wt %, more preferably at about 20 to about 70 wt %. The non-conjugated diene is incorporated into the EPDM at about 0.5 to about 15 wt %; more preferably about 1 to about 5 wt %, e.g., 3 wt %.

The term "nitrile rubber" means an acrylonitrile copolymer rubber. Suitable nitrile rubbers comprise rubbery polymers of 1,3-butadiene and about 20–50 wt % acrylonitrile. Any nitrile rubber which is a "solid" rubber having an average molecular weight of at least 50,000 and preferably between about 100,000–1,000,000 can be used. Commercially available nitrile rubbers suitable for the practice of the invention are described in *Rubber World Blue Book*, 1980 Edition, "Materials and Compounding Ingredients for Rubber", pages 386–406, which is incorporated herein by reference.

Butyl rubber is a copolymer of an isoolefin and a conjugated multiolefin. The useful copolymers comprise a major portion of isoolefin and a minor amount, preferably not more than 30 wt %, of a conjugated multiolefin. The preferred copolymers comprise about 85–99.5 wt % (preferably 95–99.5 wt %) of a $C_4$–$C_7$ isoolefin, such as isobutylene, and about 15–0.5 wt % (preferably about 5–0.5 wt %) of a multiolefin of about 4–14 carbon atoms. These copolymers are referred to in the patents and literature as "butyl rubber"; see, for example, the textbook *Synthetic Rubber* by G.S. Whitby (1954 edition by John Wiley and Sons, Inc.), pages 608–609, etc. which is incorporated herein by reference. The term "butyl rubber" as used in the specification and claims includes the aforementioned copolymers of an isoolefin having 4–7 carbon atoms and about 0.5 to 20 wt % of a conjugated multiolefin of about 4–10 carbon atoms. Preferably these copolymers contain about 0.5 to about 5% conjugated multiolefin. The preferred isoolefin is isobutylene. Suitable conjugated multiolefins include isoprene, butadiene, dimethyl butadiene, piperylene, etc.

Commercial butyl rubber is a copolymer of isobutylene and minor amounts of isoprene. It is generally prepared in a slurry process using methyl chloride as a vehicle and a Friedel-Crafts catalyst as the polymerization initiator. The methyl chloride offers the advantage that $AlCl_3$, a relatively inexpensive Friedel-Crafts catalyst is soluble in it, as are the isobutylene and isoprene comonomers. Additionally, the butyl rubber polymer is insoluble in the methyl chloide and precipitates out of solution as fine particles. The polymerization is generally carried out at temperatures of about −90C to −100C. See U.S. Pat. Nos. 2,356,128 and 2,356,129 incorporated herein by reference.

In the halogenation process, butyl rubber in solution is contacted with chlorine or bromine in a series of high-intensity mixing stages. Hydrochloric or hydrobromic acid is generated during the halogenation step and must be neutralized. For a detailed description of the halogenation process see U.S. Pat. Nos. 3,029,191 and 2,940,960, as well as U.S. Pat. No. 3,099,644 which describes a continuous chlorination process, all of which patents are incorporated herein by reference.

The rubbers used in the practice of this invention are preferably utilized in their unvulcanized state.

The preferred elastomeric core of the the film comprises a blend of ethylene propylene copolymer rubber or EP diene rubber (EPM or EPDM) and butyl type rubber (PIB or butyl rubber) in weight ratios ranging from 3:7 to 7:3, preferably 6:4 to 4:6. Although EP or butyl satisfy the extension properties, the preferred elastomeric core is comprised of a blend to provide a balance of propertis. The crystallinity of the EP rubber confers pellet stability to the blend (i.e. resists agglomeration during processing) and the butyl type rubber imparts low modulus (i.e. softness) to the film.

The core may include other additions such as slip agent, block copolymer rubber (e.g. Kraton), antioxidant, or plasticisers (e.g. refined oil).

The rubber compound ingredients may be blended in the proper weight ratio prior to introduction into the extruder.

Thermoplastic Skin Layers: Thermoplastics are distinguished from elastomers by their substantially inelastic properties. Whereas certain thermoplastics such as EVA exhibit some elasticity, the degree of elasticity falls short of that required to meet the "rubber" definition of ASTM D 1566. In general, any of the thermoplastic resins known in the prior art to be useful as films may be used as the skin layers, provided the film extrudate bonds satisfactorily to the rubber core layer. Suitable thermoplastic polymeric resins include polymers of branched and straight chained olefins such as polyethylene, polypropylene, polybutylene, polypentene, polymethylpentene and the like and various copolymers of ehtylene and copolymers of propylene.

The ethylene copolymers are particularly preferred for the skin because they adhere reasonably well to rubber and possess some elasticity, and do not detract from the overall elasticity properties of the ABA film.

The ethylene copolymers include those of ethylene and at least 5 wt % (preferably at least 10 wt %) of unsaturated esters of lower carboxylic acids or unsaturated carboxylic acids, and an alpha-olefin having 3 to 12 carbon atoms, preferably 3 to 8 carbon atoms. The preferred ethylene comonomers include butene, hexene, and vinyl acetate. Specific preferred thermoplastics are ethylene vinyl acetate (EVA) copolymers, ethylene acrylic acid (EAA) copolymers, ehtylene butyl acrylate (EBA) copolymers, ethylene methacrylate (EMA) copolymers, and low density ethylene butene or hexene copolymers (comonomers wt % of 5 to 40 and preferably of 10 to 35 wt %). The ethylene copolymers generally contain from 60 to 95 weight percent ethylene, most preferably from 65 to 90 weight percent ethylene.

The most preferred ehtylene copolymer useful in the present invention is EVA. EVA may have a vinyl acetate (VA) content between about 5% and 40% by weight, with about 10 to 35% by weight being preferred and 15 to 25% by weight being most preferred.

VA contents below about 5 wt % do not confer sufficient flexibility and orientability for purposes of the present invention and VA contents above 40 wt % exhibit excessive tackiness. The best balance of orientability and non-tackiness occurs at VA contents between 15 and 25 wt %.

Preferred Melt Index (ASTM-D-1238, Condition E) for EVA is from 0.5 to 20, with 1 to 10 being preferred and 1–5 most preferred.

It will be appreciated that the composite film may have an AB or ABC multilayer structure as well as an ABA structure described above. In the ABC multilayer, the skin layers A and C may have a different composition with skin layer A having the composition as described above. In this embodiment, the film can be formulated so that only layer A will have the desired surface profile described above.

It will also be apperciated that the composite film may be a multilayer coextruded film which comprises: (a) a core layer of an elastomeric material; and (b) at least one skin layer of a thermpolastic material, said skin layer being secured to said core layer at spaced apart contact areas and having a microundulating surface in the machine direction or transverse direction such that the film hs a gloss of less than 20 as determined by ASTM D1003-67.

Film Manufacture: The ABA film of the present invention may be manufactured by a three step process:

(1) The elastomeric resin and thermoplastic resins are coextruded to form the ABA (or ABC) composite structure. (Since no embossing rollers are required, higher line speeds are possible.)

(2) The composite film is stretched preferably in the machine direction (this stretches the ABA layers equally).

(3) The film is relaxed causing the core layer to contract much more than the skin layers, producing a rippled surface on each skin layer.

Following Step 1, the film generally has three layers bonded together and exhibits a relatively high degree of transparency since the outer surfaces of the skin are relatively smoothe. The stretching of the Step 2 may even increase the transparency since it will tend to reduce this film gauge and smoothe the film surface further.

Figure 2:
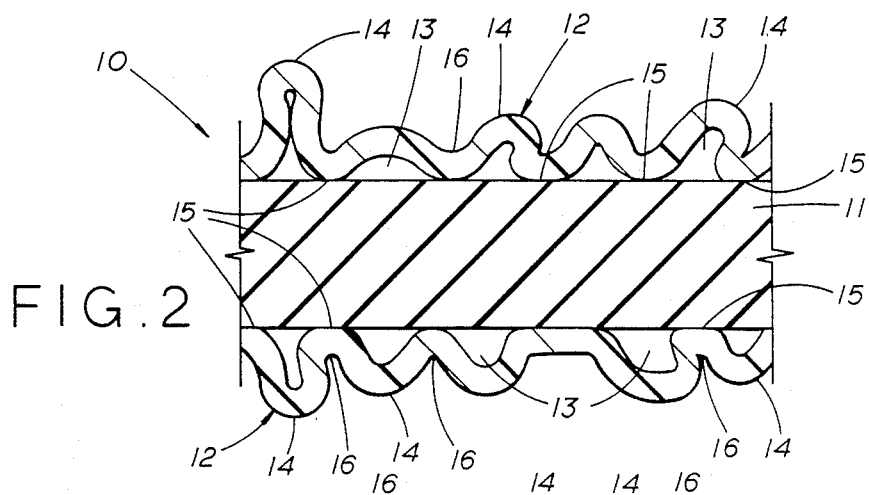
FIG. 2 is a cross sectional view of a magnified portion of the film shown in FIG. 1.
Figure 3:
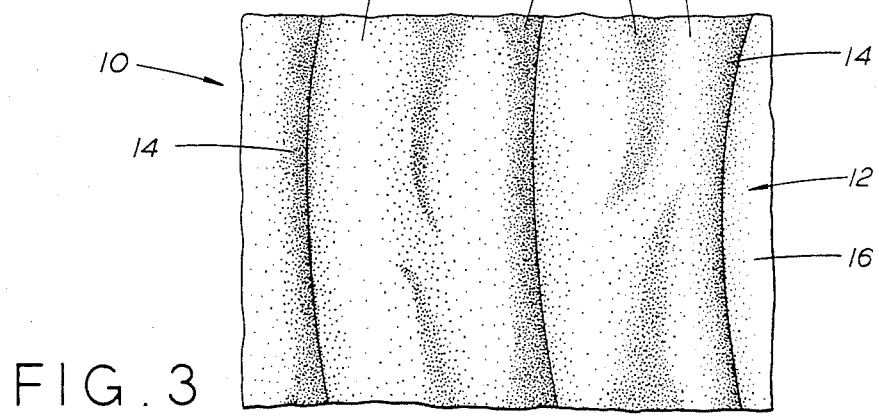
FIG. 3 is a magnified top plan view of a portion of the film shown in FIG. 2, illustrating the irregular surface.

The contraction of Step 3, surprisingly, causes the film to become hazy and imparts a silky feel to the surface. As shown in FIG. 2 (which is a drawing of a microphotograph of the film magnified 5000 times), the contraction of the elastomeric core 11 causes the thermoplastic skins 12 to separate from the surface of core 11 at spaced locations, the separations being shown as 13. This produces a rippling surface on the skins 12 wherein the ripples 14 extend generally in the transverse direction (as shown in FIG. 3) with respect to the stretch direction. It is this rippling, irregular surface on a micro scale which provides the matte finish and smoothe silky feel. The irregular surface scatters light and the reduced area contacted by the hand gives the film a silk-like feel.

Upon stretching the film again the undulations or ripples tend to disappear permitting light to be reflected uniformly from the film surface, restoring transparency.

The coextrusion of the ABA composite may be performed using conventional blending, compounding, and extruding equipment.

The stretching step may be carried out by a number of techniques. For example, with cast film two Godet rolls operating at different speeds may be used to stretch the film in the machine direction. At enter frame may be used to stretch the film in the transverse direction. The film may also be bi-directionally stretched in which case the surface undulations may intersect.

With blown film, the stretching may be achieved by the "double bubble" process which involves producing a normal blown stalk, collapsing the bubble, and reinflating the bubble to a larger diameter.

Stretching may be carried out one or more times. From one to three stretchings will be satisfactory for most films.

The degree of stretching will depend largely on the composition of the film but will be between 100% to 700% of original length, with 200 to 500% being preferred and 300% to 400% most preferred. The stretching preferably is carried out at room temperatures (65° to 80° F.).

The relaxation step may be carried out as follows. With Godet rollers, nontension take up rollers may be employed. With the tenter frame, the tenter track may be positioned to return the film to the nontension state following stretching. With blown film, relaxation is achieved by merely collapsing the bubble. The film will reach its fully relaxed state in about 5 to 10 minutes following release of the tension.

Film Properties: The film may be characterized by dimensional profile, gloss, coefficient of friction and secant modulus.

The dimensional profile of the surface of skin layer 12 may be measured by a number of instruments capable of precise surface roughness measurements. One such instrument is Surtonics 3 manufactured by Rank Tyalor Hobson. This instrument is capable of measuring in the range of 0–1000 micro inches at accuracy of ±2% of the reading.

Gloss is a measure of film transparency and is determined by ASTM D 1003-67. Gloss is represented by a numerical value range of 0–100. Films with gloss readings below 20 are low to moderate gloss films and those with readings below 10 are preferred low gloss films. Matte finish for applications such as diaper back sheets will have gloss readings of 10 or less.

Coefficient of friction (COF) were determined by ASTM D1894-78.

The tensile and tear strengths and secant modulus (which indicates softness) were determined by standard ASTM tests.

EXPERIMENTS

Materials: Samples of ABA film were prepared by coextruding core resin compound with skin resin using a Killion extruder. The core layer and skin layers had the compositions shown in Table I (all weights are wt %).

TABLE I

| FILM SAMPLE | CORE LAYER | EACH SKIN | ABA THICKNESS (%) | AVG. FILM THICKNESS (MILS) |
|---|---|---|---|---|
| A | EPM[1] (50%) Butyl Rubber[4] (50%) MI = 0.19 | EVA[6] | 9/29/9 | 3.4 |
| B | EPM[2] (50%) Butyl Rubber[4] (50%) MI = 0.20 | EVA[6] | 9/82/9 | 3.3 |
| C | EPM[3] (40%) Butyl Rubber[4] (40%) Block Copolymer[5] (20%) MI = 0.23 | EVA[6] | 9/82/9 | 2.4 |
| D | EPM[3] (35%) Butyl Rubber[4] (35%) Block Copolymer[5] (30%) MI = 0.21 | EVA[6] | 9/82/9 | 3.2 |
| E | EPM[2] (50%) Butyl Rubber[4] (50%) MI = 0.2–0.3 | EVA[7] (90%) PE[8] (10%) | 10/80/10 | 4.8 |

[1]Vistalon 3708 sold by Exxon Chemical Company
[2]Vistalon 7000 sold by Exxon Chemical Company
[3]Vistalon 719 sold by Exxon Chemical Company
[4]Butyl 065 sold by Exxon Chemical Company
[5]Kraton G-1652 sold by Shell Chemical Company
[6]LD 702.45 (0.3 MI) sold by Exxon Chemical Company 12% VA with small amounts of BHT, antiblock and slip additive.
[7]LD 721.62 (2.5 MI) 18% VA with small amounts of slip agent and antiblock.
[8]PE containing minor amounts of slip agent and antiblock additive.

The core layers of samples A,B,C, D and E also included small amounts of slip and antiblock additives. The MI of each core layer compound was determined at condition E and the units are dg/min at 190° C.

The extruder conditions were as shown in Table II.

TABLE II

|  | Skin Extruder | Core Extruder |
|---|---|---|
| Size (inches) | 0.75 | 1 |
| L/D | 24/1 | 24/1 |
| HP | 1.5 | 3.0 |
| Comp. Ratio | 3/1 | 3/1 |
| Extruder Temp. (°F.) | 350°–430° | 350°–430° |
| Melt (°F.) | 365°–375° | 419°–422° |
| RPM | 30 | 80 |
| GMS/min | 14 | 62.5–65.5 |

The film samples had the following physical properties (before stretching):

TABLE III

|  | A | B | C | D |
|---|---|---|---|---|
| Tensile Strength, psi (MD) | 1135 | 1200 | 1400 | 1635 |
| Ultimate Elongation, % (MD) | 410 | 400 | 440 | 405 |
| 1% Secant Modulus, Psi (MD) | 2500 | 2500 | 4200 | 5000 |
| Tear Strength, g/mil (MD) | 41 | 34 | 70 | 90 |

Each sample having length of 0.591 inches was tested on a Instron with maximum jaw separation of 2.5 inches and operated at a speed of 5 in./min.

The test procedure was as follows:

Stretch sample to 100% or 150% elongation and immediately remove stress.

Stretch sample three times.

Data (presented in Table IV)

Modulus, psi

Permanent Set after 3rd Cycle; % (unrecovered strain at return to zero stress divided by maximum strain after 5 min. recovery period). (Permanent set indicates the amount of recovery from a maximum extension.)

Gloss, before and after Stretching (All data taken with film sample in relaxed condition.)

TABLE IV

| | FILM SAMPLE | | | |
|---|---|---|---|---|
| | A | B | C | D |
| 100% Extension - | | | | |
| Modulus, psi | 345 | 390 | 575 | 540 |
| Permanent Set, % (1) | 17 | 18 | 10 | 17 |
| 60° Gloss | | | | |
| Unstretched | 34 | 39 | 56 | 45 |
| Relaxed Stretched Cond. (1) | 5 | 6 | 5 | 8 |

(1) After third cycle

Sample E was made in two thicknesses, a 4 mil thick film and a 8 mil thick film. The properties (before stretching) of these films are presented in Table V.

TABLE V

| | SAMPLE E | |
|---|---|---|
| | 4-mil | 8-mil |
| Tensile Strength, psi | | |
| @ Yield MD | 225 | 210 |
| TD | 155 | 160 |
| @ Break MD | 1,205 | 960 |
| TD | 705 | 650 |
| Elongation, % | | |
| @ Yield MD | 30 | 35 |
| TD | 17 | 20 |
| @ Break MD | 485 | 545 |

TABLE V-continued

| | SAMPLE E | |
|---|---|---|
| | 4-mil | 8-mil |
| TD | 645 | 600 |
| 1% Secant Modulus, psi MD | 1,765 | 1,355 |
| TD | 1,715 | 1,480 |
| Elmendorf Tear Strength, g/mil | | |
| MD | NT[(1)] | NT |
| TD | 162 | 286 |
| Haze, % - As Made | 7.7 | 17.8 |
| Haze, % - After RT Stretching | 95.0 | 95.5 |
| Permanent Set, % | | |
| 3 cycles to 100% Extension - MD | 16 | 12 |
| TD | 16 | 16 |
| 3 cycles to 150% Extension - MD | 28 | 28 |
| TD | 48 | 44 |

[(1)]NT = No Tear

Sample E films were also tested to determine the effect of stretching on the film secant modulus and COF. The stretched samples were cycled about 3 or 4 times at 200–400% of original length. The data are presented in Table VI.

TABLE VI

| | 4 mils | | 8 mils | |
|---|---|---|---|---|
| | Un-stretched | Relaxed Condition | Un-stretched | Relaxed Condition |
| 1% Secant Modulus, psi | | | | |
| MD | 1765 | 720 | 1355 | 1150 |
| TD | 1715 | 370 | 1480 | 1030 |
| COF | | | | |
| MD | >1 | 0.10 | 0.58 | 0.16 |
| TD | >1 | 0.19 | >1 | 0.58 |
| Gloss | 47.2 | 4.0 | 59.9 | 10.4 |

The surface profiles of Sample E film were measured using the Surtronic 3 instrument. Table VII presents the surface profile data. (Note stretched film data was after three cycles of 100% elongation and relaxation.)

TABLE VII

| | 4-mil Film | | | | 8-mil | | | |
|---|---|---|---|---|---|---|---|---|
| | Unstr. | | Relaxed Stretched Cond. | | Unstr. | | Relaxed Stretched Cond. | |
| | MD | TD | MD | TD | MD | TD | MD | TD |
| Ra, microinches | 50 | 24 | 96 | 84 | 37 | 25 | 70 | 73 |
| Rt, microinches | 273 | 163 | 654 | 334 | 189 | 149 | 286 | 621 |
| Rtm, microinches | 182 | 94 | 481 | 274 | 145 | 64 | 223 | 367 |
| Rpm, microinches | 92 | 48 | 247 | 145 | 64 | 34 | 115 | 191 |
| Pc peak/cm @ 75 microinches | 23 | 10 | 62 | 57 | 15 | 15 | 39 | 77 |
| tp % | | | | | | | | |
| 25 | 3 | 3 | 2 | 2 | 1 | 9 | 5 | 1 |
| 50 | 18 | 12 | 0 | 7 | 20 | 25 | 11 | 1 |
| 75 | 29 | 47 | 1 | 15 | 38 | 38 | 24 | 1 |
| 100 | 39 | 75 | — | — | 78 | 78 | — | 2 |
| 125 | — | 95 | 16 | 21 | 100 | 85 | 57 | — |
| 150 | 56 | 100 | — | — | — | 98 | — | — |
| 175 | — | — | — | — | — | 100 | 80 | 13 |
| 200 | 79 | — | 22 | 71 | — | — | 94 | — |
| 250 | 99 | — | — | — | — | — | 100 | 45 |
| 325 | — | — | 49 | 100 | — | — | — | 80 |
| 400 | — | — | 66 | — | — | — | — | 90 |

TABLE VII-continued

| | 4-mil Film | | | | 8-mil | | | |
|---|---|---|---|---|---|---|---|---|
| | Unstr. | | Relaxed Stretched Cond. | | Unstr. | | Relaxed Stretched Cond. | |
| | MD | TD | MD | TD | MD | TD | MD | TD |
| | 500 | — | — | 94 | — | — | — | — | 100 |

Ra — Height of roughness irregularities as measured by the average value of the departures from a center line drawn such that the sum of the areas above the line equals the sum of those below the line.
Rt — Maximum peak to valley height over the sample assessment length.
Rtm — Mean of the maximum peak to valley heights recorded on several passes.
Rpm — Mean of the maximum profile height above the mean line on several passes.
Pc — The peak count is the number of local peaks which project through a selectable band centered about the mean line. The count is determined only over the assessment length though the results are given in peaks per cm (or per in).

$$Pc = \frac{\text{No. of counts}}{\text{Assessment length (cm)}} = \text{Peaks/cm}$$

tp %. — Bearing ratio tp % is the length of bearing surface (expressed as a percentage of the assessment length L) at a depth p below the high peak. By making a number of measurements at different depths p, and plotting p against tp % the bearing ratio (or Abbott Firestone curve) can be drawn.

The combination of the Ra and Pc or Rpm and Pc values probably are the best measurements for the surface profile of the film. Comparing these values for the unstretched film with those of the relaxed stretched film clearly shows that both the amplitude (avg.) and the number of peaks increased as a result of the stretching and relaxation process.

The comination of Pc and tp% data indicate that although the relaxed stretched film has far more peaks (above 75) microinches, the bearing ratio is far less than the unstretched film.

It is preferred that the film of the present invention have the following roughness values, at least in one direction (MD or TD) and preferably in both directions.

| | Broad Range | Preferred Range |
|---|---|---|
| Pc @ 75 microinches | 30-100 | 50-100 |
| tp % @ 75 microinches | less than 25% (1-25%) | less than 10% (1-10%) |
| tp % @ 250 microinches | less than 90% (20-90%) | less than 50% (20-50%) |
| Ra microinches | 50-150 | 60-100 |
| Rpm microinches | 100+ | 100-300 |

From the data presented in Tables IV and VI, the following conclusions regarding the effect of stretching and relaxing the ABA film having a rubber core and thermoplastics skins may be reached:
(1) The surface roughness is increased,
(2) The gloss is decreased,
(3) The COF is reduced,
(4) The secant modulus is reduced, and
(5) The feel of the film is transformed from plastic to silky (observed).

What is claimed is:
1. A multilayer coextruded film which comprises
(a) a core layer of an elastomeric material; and
(b) at least one skin layer of a thermoplastic material, said skin layer being secured to said core layer at spaced apart contact areas and having a microundulating surface in the machine direction or transverse direction such that the film has a gloss of less than 20 as determined by ASTM D1003-67.
2. The film as defined in claim 1 wherein the microundulations of the skin layer provide a gloss of 10 or less.
3. The film of claim 2 wherein the microundulations provide the skin layer with a profile having an Rpm in excess of 100 microinches and a Pc of at least 30 peaks/cm in the machine direction or transverse direction wherein Rpm and Pc are in the same direction and wherein
   Rpm is the mean of the maximum height profile above the mean line in the machine direction or transverse direction above and below its centre line; and
   Pc is the number of local peaks which project through a 75 microinch band centered about the mean line of the surface profile of the skin layer in the machine direction or transverse direction.
4. The film of claim 3 wherein the film profile has a tp% of less than 25% at a p of 75 microinches and a tp % of less than 90% at a p of 300 microinches, wherein tp % is the bearing ratio and is the length of bearing surface expressed as a % of assessment length in the direction of Rpm and Pc at a depth of p below the highest peak.
5. The film of claim 3 wherein the skin layer has an Rpm of at least 150 microinches and a Pc of at least 50.
6. The film as defined in claim 1 wherein the elastomeric material is selected from the group consisting of PIB, EPM, EPDM, Butyl Rubber, block copolymer rubber, and mixtures of these and the thermoplastic material is a copolymer of ethylene and a comonomer selected from the group consisting of olefins having from 3 to 8 carbon atoms, vinyl acetate, methacrylic acid, acrylic acid, butyl acrylate, and mixtures of these.
7. A multilayer coextruded film comprising
(a) an elastomeric core layer; and
(b) two thermoplastic skin layers secured to opposite sides of the core layer, said skin layers being secured to the core layer at random spaced apart contact areas to provide each skin layer with microundulating configuration in the machine direction or transverse direction, said film having a gloss value less than 20 as determined by ASTM D 1003-67.
8. The film as defined in claim 7 wherein the skin layers are composed of a polyolefin selected from ethylene and propylene homopoylmers and copolymers.
9. The film is defined in claim 8 wherein each skin layer is composed of a copolymer of ethylene and a comonomer selected from the group consisting of vinyl acetate, methacrylic acid, acrylic acid, butyl acrylate, and olefins having from 3 to 8 carbon atoms, said comonomer comprising from 5 to 40 wt % of the copolymer.
10. The film as defined in claim 9 wherein the olefin is selected from the group consisting of butene and hexene wherein said olefin comprises from 10 to 35 wt % of the copolymer.

11. The film as defined in claim 7 wherein the thickness of the film is 10 mils or less and the core layer comprises from 60 to 90 wt % of the film thickness.

12. The film as defined in claim 7 wherein the film upon being stretched at least 100% of its length has substantially higher gloss than the unstretched condition.

13. The film as defined in claim 7 wherein the film has a gloss of 10 or less.

14. The film of claim 13 wherein the thermoplastic skin layers comprise EVA wherein the Va comprises from 5 to 40 wt % of the copolymer and the core layer comprises a blend of 30 to 70 wt % of EPM and 70 to 30 wt % of butyl rubber.

15. The film of claim 13 wherein the core layer comprises a rubber selected from the group consisting of EPM, butyl rubber, block copolymer rubber, and blends thereof.

16. The film as defined in claim 15 wherein the core layer comprises from
from 25 to 45 wt % of EPM,
from 25 to 45 wt % of butyl rubber, and
from 50 to 10 wt % of block copolymer rubber 17. The film of claim 15 wherein the block copolymer rubber is selected from the group consisting of styrene-ethylene- butylene-styrene and styrene-butadine-styrene block copolymer.

* * * * *